(12) United States Patent
Fries

(10) Patent No.: US 7,295,017 B2
(45) Date of Patent: Nov. 13, 2007

(54) METHOD AND SYSTEM FOR CALCULATING RAILROAD TRACK BALLAST RESISTANCE

(75) Inventor: Jeff Fries, Kansas City, MO (US)

(73) Assignee: General Electric Company, Schenectady, NY (US)

( * ) Notice: Subject to any disclaimer, the term of this patent is extended or adjusted under 35 U.S.C. 154(b) by 184 days.

(21) Appl. No.: 11/242,333

(22) Filed: Oct. 3, 2005

(65) Prior Publication Data
US 2007/0074581 A1   Apr. 5, 2007

(51) Int. Cl.
*G01R 31/08*   (2006.01)
*G01R 27/08*   (2006.01)
*B61L 1/02*   (2006.01)

(52) U.S. Cl. ............ 324/525; 324/693; 246/121

(58) Field of Classification Search ........ 324/525, 324/217, 693; 246/121
See application file for complete search history.

(56) References Cited

U.S. PATENT DOCUMENTS 3,246,143 A * 4/1966 Steele et al. ............ 246/128
3,614,418 A   10/1971 Pell
3,614,634 A   10/1971 Jones et al.
3,870,952 A * 3/1975 Sibley .................... 324/693
3,977,634 A   8/1976 Smith
4,324,376 A * 4/1982 Kuhn ..................... 246/125
2007/0132463 A1* 6/2007 Anderson ............... 324/713

* cited by examiner

*Primary Examiner*—Anjan Deb
(74) *Attorney, Agent, or Firm*—Carlos Luis Hanze, Esq.; Terry M. Sanks, Esq.; Beusse Wolter Sanks Mora & Maire, P.A.

(57) ABSTRACT

A method of estimating a resistance value for ballast, over a given length of track, used at a crossing on a railroad track that has a crossing warning system where a inductance of the track over the given length, an inductance of the track over the given length of the track, a capacitance of the track over a given length of track, and an operating frequency of the warning crossing system are all known, the method including calculating a track impedance having a magnitude and a phase angle, applying a current waveform and a voltage waveform through the track at a known frequency, measuring the phase angle, calculating a ballast resistance by using the measured phase angle in place of the calculated phase angle, the given track length, resistance over the given length of track, inductance over the given length of track, capacitance over the given length of track, and the operating frequency.

16 Claims, 5 Drawing Sheets

METHOD AND SYSTEM FOR CALCULATING RAILROAD TRACK BALLAST RESISTANCE

FIELD OF THE INVENTION

This invention relates generally to the field of rail transportation and, more particularly, to a method and system for estimating ballast resistance.

BACKGROUND OF THE INVENTION

One of the most demanding applications for crushed stone is as railroad ballast. Ballast is usually produced from natural deposits of granite, trap rock, quartzite, dolomite or limestone. Ballast serves as a bed for railroad tracks and provides track stability, drainage, and support of significant loads carried by railcars. In addition, it deters the growth of vegetation and allows for track maintenance to be performed more easily.

Near a railroad crossing, a transmitter and receiver associated with a crossing warning system apply and detect electrical signals across the tracks. These elements are used to determine when to activate a crossing protection system. A crossing protection system includes, but is not limited to, such parts as gates, bells, lights, etc.

Over time, due to environmental conditions and debris, ballast may deteriorate. Deteriorated ballast can cause instability in the railroad track. Additionally, it is possible that the deterioration may result in the ballast becoming conductive. If the deterioration results in the ballast becoming more conductive, it is possible that a crossing warning system may falsely activate a crossing protection system when a train is not approaching a road crossing. It should be noted that false activations tend to "de-sensitize" the general public to the protection provided by the crossing warning system, such that they may ignore it.

BRIEF DESCRIPTION OF THE INVENTION

The present invention solves the above-stated problems in the art by providing a system, method, software program and online computer site for calculating and monitoring railroad track ballast resistance, such that preventative maintenance can be requested to be performed on the ballast before the crossing warning system falsely activates.

Towards this end, a system for calculating ballast resistance between two parallel rails forming a railway track at a crossing is disclosed. The system has a power source device to generate a voltage waveform and a corresponding current waveform through a track at a known frequency, and a sensor to measure a phase angle between the voltage waveform and current waveform over a specified length of track. The system also has a processor connected to the sensor operable to receive data regarding the phase angle. An algorithm operable within the processor is also part of the system and is used to process the phase angle in combination with the frequency, the length of track and accepted values for track resistance over the specified length of track, track inductance over the specified length of track, and track capacitance over the specified length of track to calculate an estimated value for ballast resistance.

A method is also disclosed for estimating a resistance value for ballast, over a given length of track, used at a crossing on a railroad track that has a crossing warning system where a inductance of the track over the given length, an inductance of the track over the given length of the track, a capacitance of the track over a given length of track, and an operating frequency of the warning crossing system are all known. The method comprises calculating a track impedance having a magnitude and a phase angle, applying a current waveform and a voltage waveform through the track at a known frequency, and measuring the phase angle. The method also comprises a ballast resistance being calculated by using the measured phase angle in place of the calculated phase angle, the given track length, resistance over the given length of track, inductance over the given length of track, capacitance over the given length of track, and the operating frequency.

Another exemplary method is disclosed for determining in advance when maintenance is needed for railway ballast that is used at a crossing on a railroad track that has a crossing warning system. This method includes applying electrical power to a track, measuring a voltage waveform over a pre-determined length of the track, and measuring a current waveform over a pre-determined length of the track. A phase angle is determined based on the voltage waveform and the current waveform over the pre-determined length of the track. The phase angle data is recording over time and when the phase angle reaches a pre-determined value, a user is notified of a change in the phase angle.

A computer software program is also disclosed for use with a railroad crossing on a railroad track that has a crossing warning system having a shunt on opposite sides of the crossing, a transmitter and a receiver, with at least one computer, and a computer software code for the computer to estimate a ballast resistance of ballast used with the railroad crossing, the computer software module has a software module for a computer for retaining values for a given track length, track resistance, track capacitance, track inductance, and a given frequency, and a software module for a computer for calculating a complex railroad track impedance as a function of the given length of the track and the given frequency. A software module for a computer for measuring a phase angle of the track when a voltage waveform and corresponding current waveform is applied to the track is also included. A software module for a computer for calculating ballast resistance using the measured phase, the length of the track, the operating frequency, track resistance, track inductance and track capacitance is also included.

BRIEF DESCRIPTION OF THE DRAWINGS

The features and advantages of the present invention will become apparent from the following detailed description of the invention when read with the accompanying drawings in which.

DETAILED DESCRIPTION OF THE INVENTION

Figure 1:
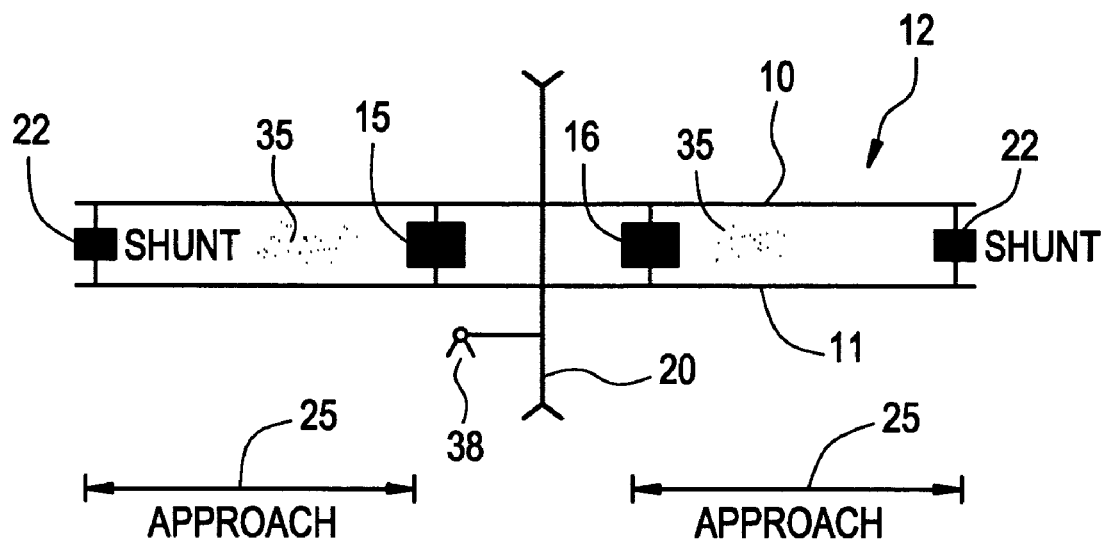
FIG. 1 is an illustration of an exemplary embodiment of a prior art crossing warning system.

Reference will now be made in detail to the embodiments consistent with the invention, examples of which are illustrated in the accompanying drawings. Wherever possible, the same reference numerals used throughout the drawings refer to the same or like parts.

The present invention solves the problems in the art by providing a system, method, and a computer software product for providing a tracking ballast resistance so as to determine when the ballast resistance is at a level where it may interfere with a crossing warning system.

The invention is primarily described as a method for estimating ballast resistance. However, persons skilled in the art will recognize that an apparatus, such as a data processing system, including a CPU, memory, I/O, program storage, a connecting bus, and other appropriate components, could be programmed or otherwise designed to facilitate the practice of the method of the invention. Such a system would include appropriate program means for executing the method of the invention.

Also, an article of manufacture, such as a pre-recorded disk or other similar computer program product, for use with a data processing system, could include a storage medium and program means recorded thereon for directing the data processing system to facilitate the practice of the method of the invention. Such apparatus and articles of manufacture also fall within the spirit and scope of the invention.

Broadly speaking, the invention provides a method, apparatus, and program for displaying ballast resistance values over time to determine when maintenance to the ballast must be accomplished. To facilitate an understanding of the present invention, it is described hereinafter with reference to specific implementations thereof. The invention is described in the general context of computer-executable instructions, such as program modules, being executed by a computer. Generally, program modules include routines, programs, objects, components, data structures, etc. that perform particular tasks or implement particular abstract data types. For example, the software programs that underlie the invention can be coded in different languages, for use with different platforms. In the description that follows, examples of the invention are described in the context of a web portal that employs a web browser. It will be appreciated, however, that the principles that underlie the invention can be implemented with other types of computer software technologies as well.

Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer storage media including memory storage devices. The technical effect of the present invention is to provide for trending resistance from ballast so as to know in advance when ballast resistance may effect operations of a crossing warning system.

The invention can be implemented in numerous ways, including as a system (including a computer processing system), a method (including a computerized method), an apparatus, a computer readable medium, a computer program product, a graphical user interface, including a web portal, or a data structure tangibly fixed in a computer readable memory. Several embodiments of the invention are discussed below.

FIG. 1 is an illustration of an exemplary embodiment of a prior art crossing warning system. Between rails 10, 11 of a railroad track 12, a transmitter 15 and receiver 16 are located near a road crossing 20. In either direction a train may travel on the railroad track, an electrical shunt 22 is positioned. The electrical shunts 22 are tuned to the operating frequency of the transmitter 15. The electrical shunts 22 are at a further distance from the crossing 20 than the transmitter 15 and receiver 16. The shunts 22 define a fixed length track circuit, known as a crossing approach 25. The crossing approaches define a surveillance area in which train motion is detected. By having a defined surveillance area the crossing protection system is activated a constant time prior to a train arriving at the road crossing 20, regardless of train speed or direction from which the train approaches.

Figure 2:
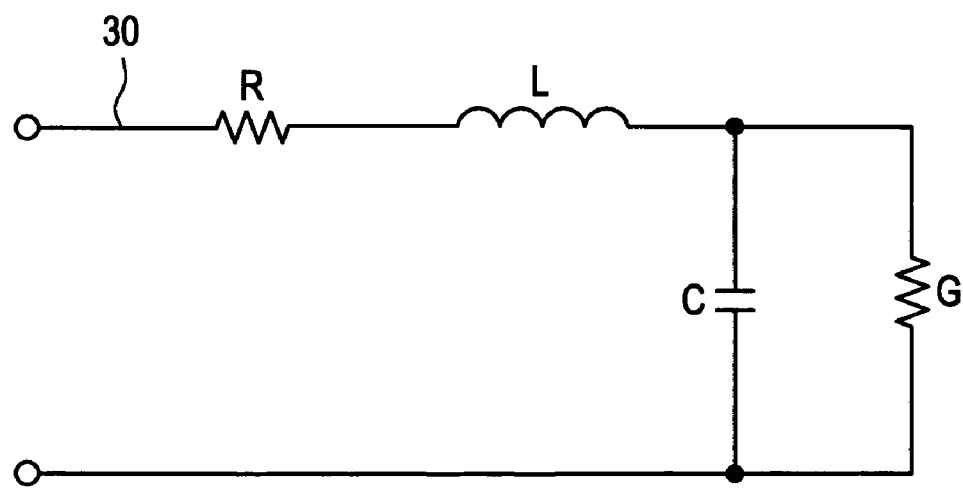
FIG. 2 is an illustration of an exemplary embodiment of a schematic representing a railroad track and an element representative for rail to rail ballast resistance.

FIG. 2 is an illustration of an exemplary embodiment of an electrical schematic representing a railroad track. As illustrated, the railroad track 12 are electrically modeled as a collection of transmission line elements, or lumps 30. The lump 30 consists of a series resistance R, series inductance L, shunt capacitance C, and a shunt conductance G. The shunt conductance G can be equated to the rail-to-rail ballast resistance. As applied to a two-rail track, half of the value for the series resistance R and series inductance L comes from one rail and the other half of these elements come from the second rail. A lump 30 can be measured over a certain length, such as per foot increments. Depending on the length of track being evaluated, the values are then multiplied by that length of track, such as 1000 feet.

Using standard transmission line equations, the complex railroad track impedance can be calculated as a function of length Y, and operating frequency F as shown below:

$$Ztrack = \left(\frac{e^{\tau \cdot Y} - e^{-\tau \cdot Y}}{e^{\tau \cdot Y} + e^{-\tau \cdot Y}}\right) \cdot Zo$$

where $$Zo = \sqrt{\frac{(R + j \cdot 2 \cdot \pi \cdot F \cdot L)}{(G + j \cdot 2 \cdot \pi \cdot F \cdot C)}}$$

$$\tau = \sqrt{(R + j \cdot 2 \cdot \pi \cdot F \cdot L) \cdot (G + j \cdot 2 \cdot \pi \cdot F \cdot C)}$$

Thus, referring back to FIG. 1, the length Y is the Approach 25. Ztrack stands for the complex impedance of the track 12. As illustrated in FIG. 2, the values for R, L, and C are fixed values based on the type and construction of rail used. F is the operating frequency of an electrical signal applied to the track circuit by transmitter 15.

Once the above equation is solved, a complex number with a real and imaginary part, or polar form a magnitude and phase angle (or phase), results. The phase represents the phase of the track impedance. The actual phase can be measured as the phase shift between a voltage and current applied to the rail 12 by the transmitter 15. By measuring the phase, a value for the shunt conductance G can be determined.

The value for G is likely to vary location to location, as well as with environmental factors. In other words, the value of G at one crossing 20 is not necessarily going to be equivalent to the value of G at another crossing. Regardless of location, the present invention measures changes in G to anticipate when the ballast resistance has changed. For example, suppose that the ballast 35 at a given crossing 20 is 15 Ohms per thousand feet. Over time, the value drops to 2 Ohms per thousand feet. Based on this drop, this crossing may be identified as a location where the ballast resistance may interfere with the operation of the crossing warning system 38. Thus, if the measured phase of the complex railroad track impedance, length of the track circuit 25, and the operating frequency are known, the ballast resistance can be determined.

Figure 3:
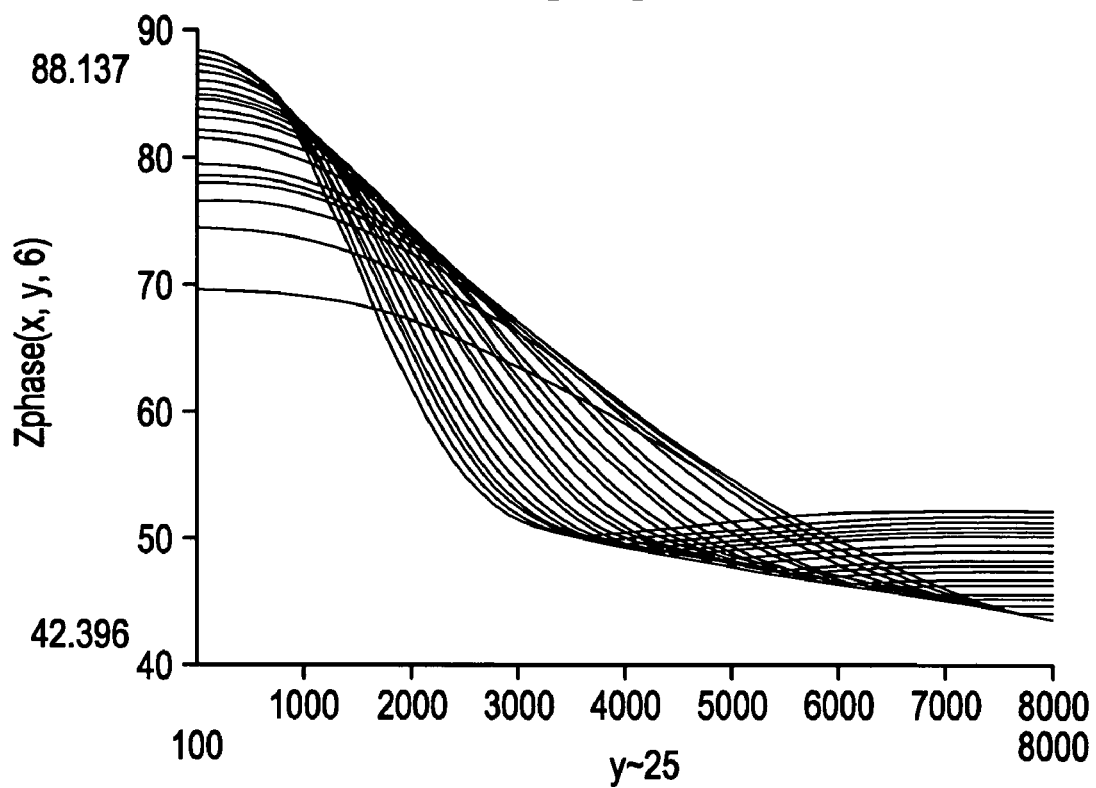
FIG. 3 is an illustration of an exemplary embodiment of a chart representing a range of phase of a given track circuit varying non-linearly based on track circuit length and operating frequency.

The phase of the complex railroad track impedance is relatively proportional to the ballast resistance. In other words, as the phase decreases, the ballast resistance decreases. The range of values for phase, as illustrated in FIG. 3, can vary non-linearly based on track length 25 and operating frequency. However, the ballast resistance is unaffected by the operating frequency, as it is a resistive property, and will scale linearly with track length 25. Thus, this makes ballast resistance a good indicator of the quality of the track circuit and when preventative maintenance may be required.

Figure 4:
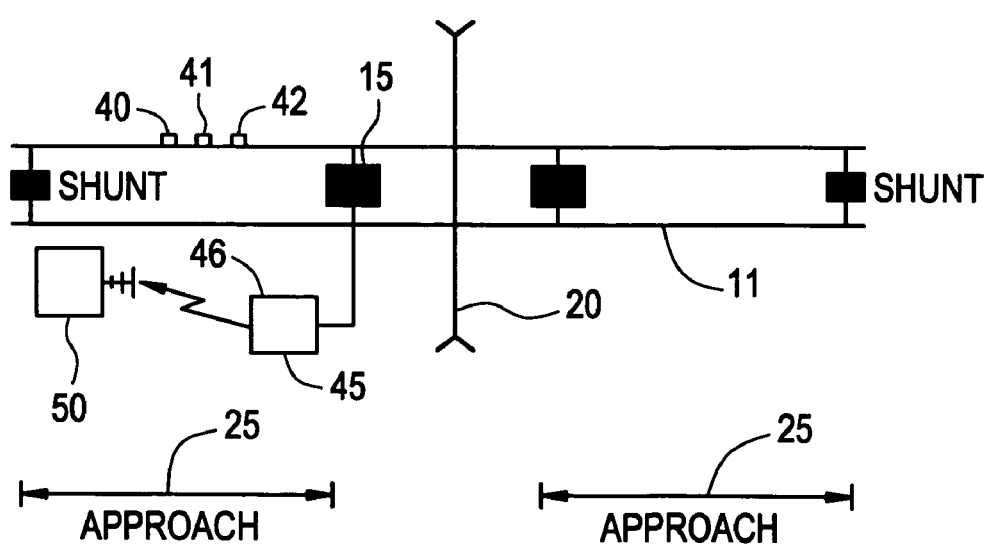
FIG. 4 is an illustration of an exemplary embodiment of the present invention.

As illustrated in FIG. 4, a system implementing the present invention includes sensors 40, 41, 42 to measure rail resistance R, inductance L, and capacitance C over a given length of track 25 where a frequency is also a fixed value. Those skilled in the art will recognize that a single sensor can be used to measure all three values. In another exemplary embodiment these values are not measured but are instead based on accepted values, such as industry acceptable values. Thus, sensors are not needed to measure these values and these values are simply provided to the algorithm as discussed below.

A voltage waveform and corresponding current waveform are applied to the track wherein the complex track impedance phase is measured based on the phase shift between the voltage and current waveforms. In an exemplary embodiment the current and voltage are supplied through the transmitter 15. In other exemplary embodiments a second power source is provided to supply the current and voltage. These values are supplied to a processor 45 that includes an algorithm 46 with exemplary equations to determine ballast resistance. The exemplary equations are derived using standard transmission line equations, such as disclosed above. Examples of these exemplary equations for given frequency ranges and approach lengths are as follows:

For Frequency=86 Hz-211 Hz and Approach Length=500 Ft-1000 Ft, $$B := \frac{1}{\begin{aligned}&k0 + k1 \cdot P + k2 \cdot A - k3F - k4P \cdot A + \\ &k5P \cdot F + k6A \cdot F - k7 \cdot P^2 + k8A^2 - \\ &k9F^2 - k10P \cdot A \cdot F + k11P^2 \cdot A - \\ &k12P \cdot A^2 + k13A^2 \cdot F + k14A \cdot F^2 + k15F^3\end{aligned}}$$

k0:=−85.07291
k1:=3.0633256
k2:=0.1302539
k3:=4.786210$^{-2}$
k4:=4.5004610$^{-3}$
k5:=5.793880$^{-3}$
k6:=2.151960$^{-4}$
k7:=3.0538960$^{-2}$
k8:=6.805030$^{-6}$
k9:=1.549710$^{-3}$
k10:=6.057210$^{-6}$
k11:=4.033530$^{-5}$
k12:=1.096270140$^{-7}$
k13:=1.5421061120$^{-8}$
k14:=5.819030$^{-7}$
k15:=1.932490$^{-6}$

For Frequency=86 Hz-211 Hz and Approach Length=1001 Ft-2000 Ft, $$B := \frac{1}{\begin{aligned}&k0 - k1 \cdot P - k2 \cdot A + k3F + k4P \cdot A + \\ &k5P \cdot F - k6A \cdot F + k7 \cdot P^2 + k8A^2 - \\ &k9F^2 - k10P \cdot A \cdot F - k11P \cdot A^2 + \\ &k12A^2 \cdot F - k13P \cdot F^2 \cdot F + k14A \cdot F^2 - k15A^3 + 16F^3\end{aligned}}$$

k0:=28.524038
k1:=0.528548
k2:=0.019059
k3:=0.0283755
k4:=2.978270$^{-4}$
k5:=1.3501810$^{-3}$
k6:=2.035970$^{-5}$
k7:=4.011810$^{-4}$
k8:=4.220350$^{-6}$
k9:=3.980410$^{-4}$
k10:=3.190440$^{-7}$
k11:=5.576650$^{-8}$
k12:=4.563210$^{-9}$
k13:=1.678930$^{-6}$
k14:=7.972850$^{-8}$
k15:=1.237830$^{-10}$
k16:=7.451210$^{-7}$

For Frequency=86 Hz-211 Hz and Approach Length=2001 Ft-3500 Ft, $$B := \frac{1}{\begin{aligned}&k0 - k1 \cdot P - k2 \cdot A - k3F + k4P \cdot A + \\ &k5P \cdot F - k6A \cdot F + k7 \cdot P^2 + k8A^2 - \\ &k9F^2 - k10P \cdot A \cdot F - k11P \cdot A^2 - \\ &k12P^2 \cdot F - k13P \cdot A^2 + k14A^2 \cdot F - \\ &k15P \cdot F^2 + k16A \cdot F^2 - k17P^3 - k18A^3 + k19\end{aligned}}$$

k0:=20.652509
k1:=0.520215
k2:=6.641$10^{-3}$
k3:=7.3088$10^{-5}$
k4:=1.08642$10^{-4}$
k5:=5.42162$10^{-4}$
k6:=1.77784$0^{-6}$
k7:=3.976357$0^{-3}$
k8:=8.36891$0^{-7}$
k9:=1.13071$0^{-4}$
k10:=7.22541$0^{-8}$
k11:=2.58163$0^{-7}$
k12:=3.89916$0^{-7}$
k13:=8.66727$0^{-9}$
k14:=3.91796$0^{-10}$
k15:=5.53964$0^{-7}$
k16:=1.32997$0^{-8}$
k17:=1.47712$0^{-5}$
k18:=2.88658$0^{-11}$
k19:=2.17036$0^{-7}$

For Frequency=86 Hz–211 Hz and Approach Length=3501 Ft–10000 Ft, $$B := (k0 + k1 \cdot P - k2 \cdot A - k3 \cdot F + k4 \cdot A + k5 \cdot P \cdot F - k6 \cdot A \cdot F - k7 \cdot P^2 + k8 \cdot F^2 + k9 \cdot P \cdot A \cdot F - k10 \cdot P^2 \cdot F + k11 \cdot P \cdot F^2 + k12 \cdot P^3 - k13 \cdot F^3)^2$$

k0:=−15.82492
k1:=1.1539402
k2:=1.23834$10^{-4}$
k3:=0.048147
k4:=1.13305$10^{-5}$
k5:=2.142$10^{-3}$
k6:=3.62267$10^{-6}$
k7:=0.02718192
k8:=3.2596$10^{-5}$
k9:=7.51537$10^{-8}$
k10:=4.91148$10^{-5}$
k11:=7.98512$10^{-6}$
k12:=2.3118$10^{-4}$
k13:=8.62743$10^{-7}$

A plurality of equations may be used in cases where a single equation is not suitable for use across all possible combination of approach length 25 and frequency. Crossing equipment approach length versus frequency setup tables might be used as a guideline for establishing realistic combinations of approach length 25 and frequency.

In one exemplary embodiment the processor 45 evaluates the ballast resistance and when the values reach a certain pre-defined level, the processor sends a warning to a central office 50 that maintenance is required at that particular railroad crossing 20. In another exemplary embodiment, ballast resistance values are constantly transmitted to the central office 50 wherein the central office 50 monitors the ballast resistance values, either manually or with a second processor. A voltage and current are generated by an electrical source, such as the transmitter 15 and are applied to the track. A phase is measured. From these measurements, G is determined. G is tracked over time to determine if changes in its value indicate maintenance of the ballast is required.

Figure 5:
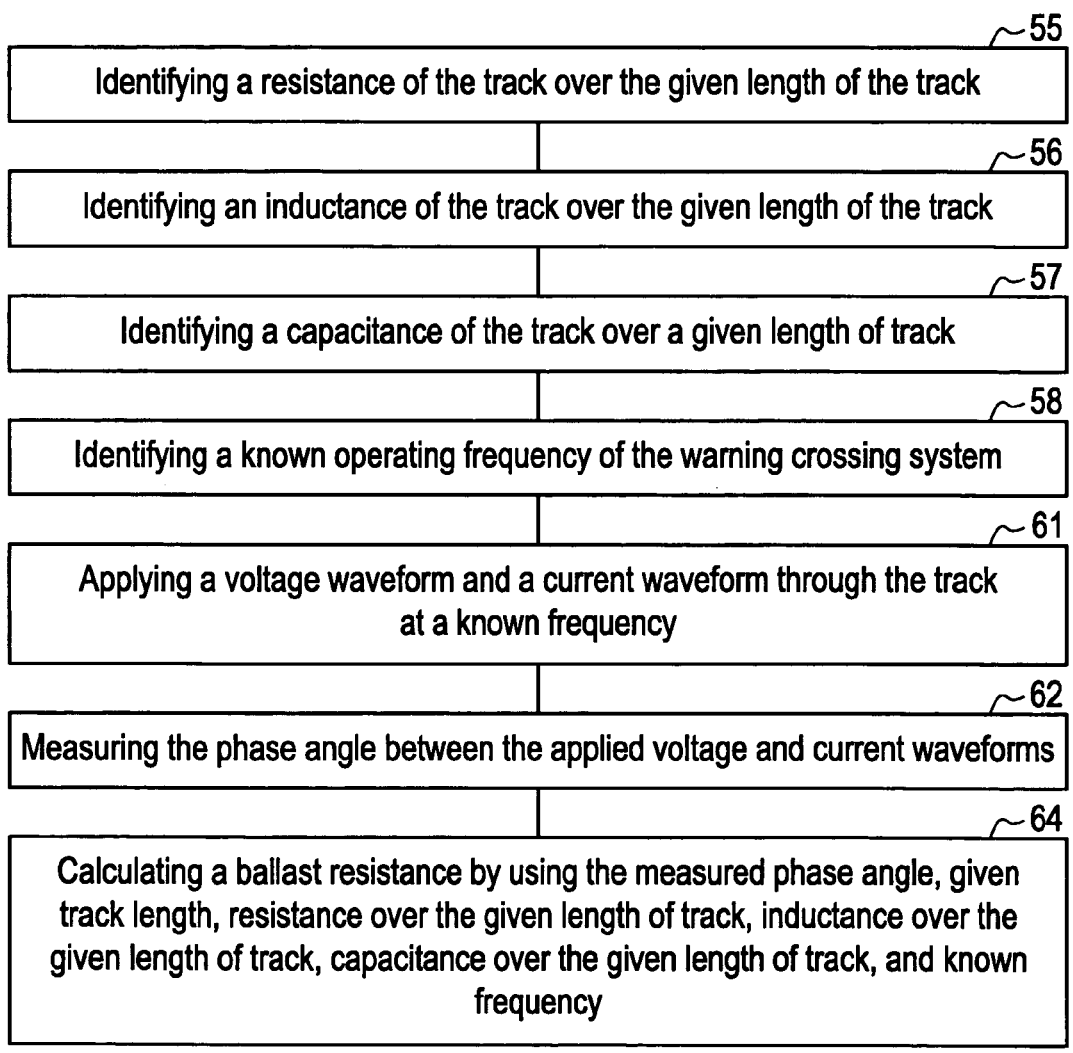
FIG. 5 is an illustration of an exemplary embodiment of steps of the present invention.

Thus, in operation, as illustrated in FIG. 5, R, L, and C are identified for a given track length 25 where a frequency is also a fixed value, steps 55, 56, 57, 58. A voltage waveform and current waveform are applied to the track at a known frequency, step 61. The complex track impedance phase is measured based on the voltage and current applied, step 62. In an exemplary embodiment, the transmitter 15 applies the voltage and current. Utilizing the known values of R, L, C, length of the approach 25, operating frequency, and the measured value of track phase, a shunt conductance G, or ballast resistance, is determined, step 64. When the shunt conductance G reaches a predefined level over time, a warning regarding deteriorated ballast is issued.

Figure 6:
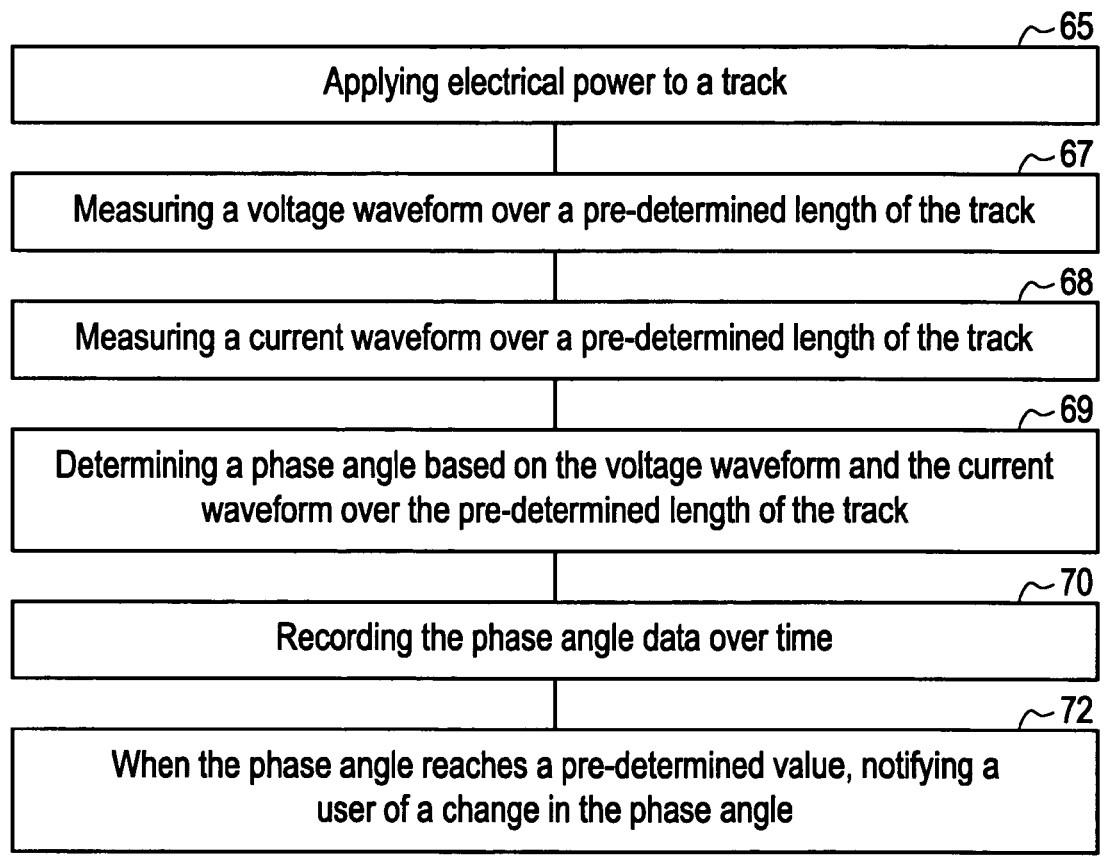
FIG. 6 is an illustration of an exemplary embodiment of the steps for determining in advance when maintenance is needed.

As illustrated in FIG. 6, a method of determining in advance when maintenance is needed for railway ballast at a crossing is disclosed. The method comprises applying electrical power to a track, step 65. A voltage waveform and a corresponding current waveform are measured over a pre-determined length of the track, steps 67, 68. A phase angle over the pre-determined length of track is determined, step 69. The phase angle data is recorded over time, step 70. When the phase angle reaches a pre-determined value, a user is notified of a change in the phase angle, step 72.

The present invention can be utilized through a computer program product. The computer program product is recorded on computer readable medium and operational on a computer for providing a composite display of data and providing a customized graphical user interface to the user, wherein the graphical user interface displays data elements arranged as a display, each of the data elements representative of ballast resistance and/or the values of the elements that are used in determining the ballast resistance. As a computer readable medium containing program instructions, an embodiment of the invention includes computer readable code devices for interacting with a user as noted above, processing that data, and generating printed or electronic media for that user.

Part or all of the data can also be sent electronically and maintained on a web server for confidential access with typical browsers. The data may also be transmitted and viewed by other well-known techniques such as email, interactive television, and the like.

Figure 7:
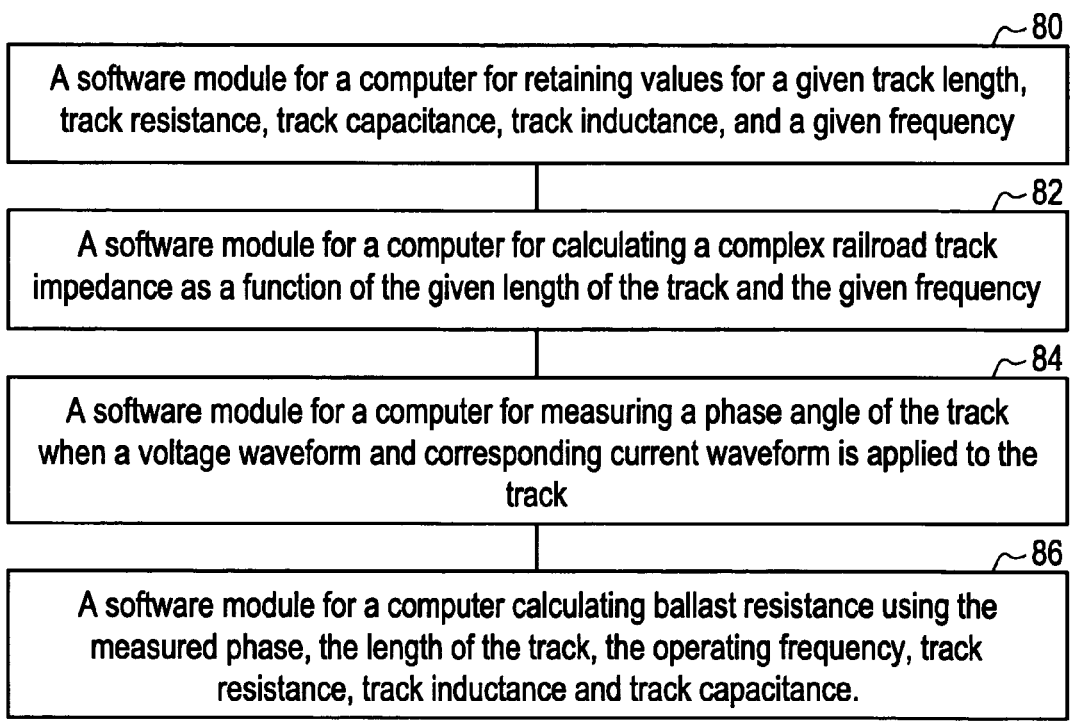
FIG. 7 is an illustration of an exemplary embodiment of the steps used in a computer software module for use with a railroad crossing.

FIG. 7 is an exemplary embodiment of a computer software module for use in a railroad crossing on a railroad track that has a warning crossing system having a shunt on opposite sides of the crossing, a transmitter and a receiver, sensors to measure resistance, capacitance, and inductance over a given length of the track, with at least one computer, and a computer software code for a computer to estimate a ballast resistance of ballast used with the railroad crossing. The software program has a software module for processing the measured resistance, capacitance, and inductance over a given length of the track, step 80. A software module for calculating a complex railroad track impedance as a function of the given length of the track and an operating frequency of the transmitter is provided, step 82. Another software module provided is for measuring a phase angle of the track, step 84. A software module for using the measured phase, the length of the track, the operating frequency, calculating ballast resistance is also provided, step 86.

While the invention has been described in what is presently considered to be a preferred embodiment, many variations and modifications will become apparent to those skilled in the art. Accordingly, it is intended that the invention not be limited to the specific illustrative embodiment but be interpreted within the full spirit and scope of the appended claims.

What is claimed is:

1. A system for calculating ballast resistance between two parallel rails forming a railway track at a crossing, the system comprising:

a) a power source device to generate a voltage waveform and a corresponding current waveform through a track at a known frequency;

b) a sensor to measure a phase angle between the voltage waveform and current waveform over a specified length of track;

c) a processor connected to the sensor operable to receive data regarding the phase angle; and d) an algorithm operable within the processor to process the phase angle in combination with the frequency, the length of track and accepted values for track resistance over the specified length of track, track inductance over the specified length of track, and track capacitance over the specified length of track to calculate an estimated value for ballast resistance.

2. The system of claim 1 further comprising a monitoring device in communication with the processor to determine when the estimated value for ballast resistance is outside of a pre-defined acceptable ballast resistance range.

3. The system of claim 1 wherein the phase angle is proportional to the estimated value of the ballast resistance.

4. The system of claim 1 further comprising a storage device to store at least one of the known frequencies, the track length being used to measure the phase angle, a value for the track resistance over the specified length of track, a value for the track inductance over the specified length of track, a value for the track capacitance over the specified length of track, and the estimated value for ballast resistance as calculated over time.

5. The system of claim 1 further comprising a notification device to inform a user when the estimated ballast resistance is estimated outside of a pre-determined range.

6. The system of claim 1 wherein the algorithm comprises a transmission line equation used to determine the ballast resistance.

7. The system of claim 1 wherein the pre-determined value is based on an original estimated ballast resistance which is then monitored over time to determine whether subsequent estimated ballast resistance values deviate by a certain factor from the original estimated ballast resistance.

8. A method of estimating a resistance value for ballast, over a given length of track, used at a crossing on a railroad track that has a crossing warning system where a inductance of the track over the given length, an inductance of the track over the given length of the track, a capacitance of the track over a given length of track, and an operating frequency of the warning crossing system are all known, the method comprising:

a) calculating a track impedance having a magnitude and a phase angle;

b) applying a current waveform and a voltage waveform through the track at a known frequency;

c) measuring the phase angle;

d) calculating a ballast resistance by using the measured phase angle in place of the calculated phase angle, the given track length, resistance over the given length of track, inductance over the given length of track, capacitance over the given length of track, and the operating frequency.

9. The method of claim 8 further comprising trending the calculated ballast resistance over time and if the value changes a predetermined amount notifying a user.

10. The method of claim 8 wherein the step of calculating a track impedance further comprises calculating the track impedance with a transmission line equation.

11. The method of claim 8 wherein the step of calculating a ballast resistance further comprises calculating the ballast resistance with a transmission line equation.

12. A method of determining in advance when maintenance is needed for railway ballast that is used at a crossing on a railroad track that has a crossing warning system, the method comprising:

a) applying electrical power to a track;

b) measuring a voltage waveform over a pre-determined length of the track;

c) measuring a current waveform over a pre-determined length of the track;

d) determining a phase angle based on the voltage waveform and the current waveform over the pre-determined length of the track;

e) recording the phase angle data over time; and f) when the phase angle reaches a pre-determined value, notifying a user of a change in the phase angle.

13. The method of claim 12 wherein the phase angle is proportional to ballast resistance.

14. In a railroad crossing on a railroad track that has a crossing warning system having a shunt on opposite sides of the crossing, a transmitter and a receiver, with at least one computer, and a computer software code for the computer to estimate a ballast resistance of ballast used with the railroad crossing, the computer software module comprising:

a) a software module for a computer for retaining values for a given track length, track resistance, track capacitance, track inductance, and a given frequency;

b) a software module for a computer for calculating a complex railroad track impedance as a function of the given length of the track and the given frequency;

c) a software module for a computer for measuring a phase angle of the track when a voltage waveform and corresponding current waveform is applied to the track; and d) a software module for a computer for calculating ballast resistance using the measured phase, the length of the track, the operating frequency, track resistance, track inductance and track capacitance.

15. The computer software module of claim 14 further comprising a software module for a computer for comparing the calculated ballast resistance over time to determine if the calculated ballast resistance value is at least one of above or below a pre-determined ballast resistance value range.

16. The computer software module of claim 14 further comprising a software module for a computer for notifying a user when the calculated ballast resistance is at least one of above or below the pre-determined ballast resistance value range.

* * * * *